United States Patent
Chernyak (10) Patent No.: US 8,025,400 B2
(45) Date of Patent: Sep. 27, 2011

(54) PUPILOMETER FOR PUPIL CENTER DRIFT AND PUPIL SIZE MEASUREMENTS AT DIFFERING VIEWING DISTANCES

(75) Inventor: Dimitri Chernyak, Sunnyvale, CA (US)

(73) Assignee: AMO Manufacturing USA, LLC, Santa Ana, CA (US)

(*) Notice: Subject to any disclaimer, the term of this patent is extended or adjusted under 35 U.S.C. 154(b) by 0 days.

(21) Appl. No.: 12/731,959

(22) Filed: Mar. 25, 2010

(65) Prior Publication Data
US 2010/0231857 A1 Sep. 16, 2010

Related U.S. Application Data

(63) Continuation of application No. 12/197,774, filed on Aug. 25, 2008, now Pat. No. 7,708,405, which is a continuation of application No. 11/088,010, filed on Mar. 22, 2005, now Pat. No. 7,431,455.

(51) Int. Cl.
*A61B 3/10* (2006.01)
*A61B 3/14* (2006.01)
(52) U.S. Cl. ................... 351/205; 351/210; 351/221
(58) Field of Classification Search .......... 351/204–206, 351/208–211, 216–218, 221
See application file for complete search history.

(56) References Cited

U.S. PATENT DOCUMENTS

| 5,094,521 A | 3/1992 | Jolson et al. |
|---|---|---|
| 5,684,561 A | 11/1997 | Yancey |
| 5,784,145 A | 7/1998 | Ghodse et al. |
| 5,790,235 A | 8/1998 | Kirschbaum |
| 5,835,192 A | 11/1998 | Roffman et al. |
| 6,090,051 A | 7/2000 | Marshall |
| 6,159,202 A | 12/2000 | Sumiya et al. |
| 6,217,172 B1 | 4/2001 | Shibutani et al. |
| 6,257,721 B1 | 7/2001 | Hayashi et al. |
| 6,260,968 B1 | 7/2001 | Stark et al. |
| 6,322,216 B1 | 11/2001 | Yee et al. |

(Continued)

FOREIGN PATENT DOCUMENTS

EP 1 038 495 A2 9/2000

(Continued)

OTHER PUBLICATIONS

Supplementary Search Report and Opinion of European Patent Application No. 06720969.2, mailed Aug. 19, 2010, 7 pages total.

*Primary Examiner* — Dawayne A Pinkney
(74) *Attorney, Agent, or Firm* — Kilpatrick Townsend and Stockton LLP (57) ABSTRACT

The present invention generally provides improved devices, systems, and methods for measuring characteristics of at least one eye, and particularly for measuring the physiological changes in eyes under different viewing conditions. An exemplary embodiment provides a pupilometer which measures any changes in location of a pupil center with changes in viewing distances. As the eye often moves significantly during viewing, the pupil center location will often be measured relative to a convenient reference of the eye such as an outer iris boundary. Pupil size may also be recorded, and the measurements from both eyes of a patient may be taken simultaneously. Exemplary embodiments may be configured so as to allow the vergence angle between the eyes to vary with differing viewing distances, regardless of whether one or both eyes are being measured.

36 Claims, 4 Drawing Sheets

U.S. PATENT DOCUMENTS

| | | |
|---|---|---|
| 6,497,483 B2 | 12/2002 | Frey et al. |
| 6,569,154 B2 | 5/2003 | Campin et al. |
| 6,820,979 B1 | 11/2004 | Stark et al. |
| 6,929,638 B2 | 8/2005 | Gray et al. |
| 7,293,873 B2 | 11/2007 | Dai et al. |
| 7,377,643 B1 * | 5/2008 | Chock et al. ............ 351/208 |
| 7,387,387 B2 | 6/2008 | Dai |
| 7,431,455 B2 | 10/2008 | Chernyak |
| 7,625,087 B2 | 12/2009 | Taylor et al. |
| 7,708,405 B2 | 5/2010 | Chernyak |
| 2003/0086057 A1 | 5/2003 | Cleveland |
| 2003/0120266 A1 | 6/2003 | Fujieda |
| 2004/0156019 A1 | 8/2004 | Masaki |
| 2004/0169817 A1 | 9/2004 | Grotehusmann et al. |
| 2004/0218142 A1 | 11/2004 | Wakil et al. |
| 2005/0174536 A1 | 8/2005 | Hanaki et al. |
| 2005/0280777 A1 * | 12/2005 | Dai ............................ 351/246 |
| 2006/0215113 A1 | 9/2006 | Chernyak |

FOREIGN PATENT DOCUMENTS

| | | |
|---|---|---|
| EP | 1 302 153 A1 | 4/2003 |
| WO | WO 2006/032920 A2 | 3/2006 |

* cited by examiner

PUPILOMETER FOR PUPIL CENTER DRIFT AND PUPIL SIZE MEASUREMENTS AT DIFFERING VIEWING DISTANCES

CROSS-REFERENCE TO RELATED APPLICATIONS

The present application is a continuation of U.S. Ser. No. 12/197,774 filed Aug. 25, 2008 (Allowed), which application is a continuation of U.S. Ser. No. 11/088,010 filed Mar. 22, 2005 (now U.S. Pat. No. 7,431,455); the disclosures, each of which are incorporated herein by reference in their entirety.

BACKGROUND OF THE INVENTION

This invention generally relates to optical diagnosis and measurements of the eye, and in particular embodiments provides devices, systems, and methods for measuring the changes in pupil position, location, and the like with changes in distance and/or other viewing conditions.

Presbyopia is a condition that affects the accommodation properties of the eye. As objects move closer to a young, properly functioning eye, ciliary muscle contraction and zonular relaxation allow the lens of the eye to become rounder or more convex. This increases the optical power of the lens and enhances the ability of the eye to focus at near distances. Accommodation can allow the eye to focus and refocus between near and far objects.

Presbyopia normally develops as a person ages, and is associated with a natural progressive loss of accommodation (sometimes referred to as "old sight"). The presbyopic eye often loses the ability to rapidly and easily refocus on objects at varying distances. There may also be a loss in the ability to focus on objects at near distances. Although the condition progresses over the lifetime of an individual, the effects of presbyopia usually become noticeable about the age of 45 years. By the age of 65 years, the crystalline lens has often lost almost all elastic properties and has only limited ability to change shape. Residual accommodation refers to the amount of accommodation that remains in the eye. A lower degree of residual accommodation contributes to more severe presbyopia, whereas a higher amount of residual accommodation correlates with less severe presbyopia.

Work is now underway on developing methods and devices for treating presbyopia. These treatments often seek to provide vision approaching that of an emmetropic eye. In an emmetropic eye, both distant objects and near objects can be seen using the accommodation of the eye. To address the vision problems associated with presbyopia, traditional treatments have included reading glasses and the like. Reading glasses add plus power diopter to the eye of an individual, thus allowing the eye to focus on near objects and maintain a clear image. Presbyopia has also been treated with bifocal eyeglasses, where one portion of the lens is corrected for distance vision and another portion of the lens is corrected for near vision. Although such approaches can provide clear vision when the eye is looking through the appropriate lens, other objects in the field of view may be distorted. Still further alternative treatments have been employed, including monovision (in which one eye is corrected for distance vision while the other eye is corrected for near vision) and the like. Many of these therapies have been successful for at least some patients, but none has been shown to provide ideal viewing capabilities for all patients throughout a wide viewing distance range.

In the field of refractive surgery, certain ablation profiles have been suggested for treatment of presbyopia. The goal of these presbyopia ablation profiles is often to increase the range of focus of the eye, rather than attempting to restore a combination. Many of these ablation profiles can provide a wider depth of focus, although in many cases with some compromise. U.S. patent application Ser. No. 10/738,358, filed on Dec. 5, 2003 and entitled "Presbyopia Correction Using Patient Data", the full disclosure of which is incorporated herein by reference, describes promising approaches for treatment of presbyopia using laser ablation and other refractive correction techniques. Many of these proposed refractions are adjusted or tailored for a specific patient.

While the newly-proposed presbyopia treatment approaches show great promise, still further enhancements in the field would be helpful. In particular, presbyopia treatments may benefit from increased knowledge regarding the response of the eye to different viewing conditions. This may, for example, facilitate developing appropriate classes of treatment shapes through a better understanding of typical physiological changes to the eye when the patient changes between viewing at near and far distances. Improved devices for measuring the eye's response to changes in viewing distances may also help tailor or select appropriate treatments for a particular patient, or may be used to exclude certain patients from treatments which would be inappropriate and/or result in visual acuities that are less than may otherwise be available through alternative treatments.

In light of the above, it would be advantageous to provide improved devices, systems, and methods for measuring and/or diagnosing eyes. It would be particularly advantageous if these improved techniques facilitated developing and/or tailoring of refractive correction prescriptions for classes of patients or individual patients.

BRIEF SUMMARY OF THE INVENTION

The present invention generally provides improved devices, systems, and methods for measuring characteristics of at least one eye, and particularly for measuring the physiological changes in eyes under different viewing conditions. An exemplary embodiment provides a pupilometer which measures changes in location of a pupil center with changes in viewing distance. As the eye tends to move significantly (voluntarily and/or involuntarily), the pupil center location will often be measured relative to a convenient reference of the eye such as an outer iris boundary. Pupil size may also be recorded, and the measurements from both eyes of a patient may be measured substantially simultaneously. Exemplary embodiments may be configured so as to allow the vergence angle between the eyes to vary with differing viewing distances, regardless of whether one or both eyes are being measured.

In a first aspect, the invention provides a pupilometer comprising an optical sensor. A sensing optical path couples the sensor with an eye measurement location. A variable distance viewing target system is coupled to a processor, which is also coupled to the sensor. The processor is thereby capable of determining a relationship between changes in viewing distance between the eye location and the viewing target and pupil center drift of a pupil of an eye disposed at the eye location.

In many embodiments, the processor will be configured to determine the relationship between changes in viewing distance and pupil center drift. The viewing target will often have an associated near viewing configuration and an associated far viewing configuration, the target in the far viewing configuration being optically separated from the eye by a greater viewing distance than in the near viewing configuration. The viewing target with the near viewing configuration will typically be optically separated from the eye by no more than about one meter. The viewing target with the far viewing configuration will typically be optically separated from the eye by at least three meters, often by five meters or more. One or more intermediate viewing distance configurations may also be provided, with the viewing distances optionally being variable throughout a range.

In many embodiments, the viewing target will be coupled to the eye measurement location by at least a portion of the sensing optical path. This can facilitate measurements from along the optical axis of the eye. In some embodiments, a target optical path will couple the target to the eye measurement position, with at least a portion of the target optical path being offset from the sensing optical path. An optical path length of the target optical path will typically vary with changes in configuration of the viewing target system. In some embodiments, the target optical path and the sensing optical path may be separated along substantially their entire length, particularly when using off-axis pupil measurements.

The changes in configuration of the viewing target may be effected by any of a variety of path length altering approaches including movable target images, a plurality of alternatively selectable target images having differing target optical path lengths, an optical zoom, a turret of alternative selectable optical elements such as different mirror assemblies, lenses or lens sets, or the like. By using zoom lenses and the like, the physical distance between the target and eye need not change.

Optionally, the pupilometer may comprise a binocular structure having an at least partially separate sensing optical path coupled to another eye measurement location for measurements of the patient's other eye. The processor can be configured to determine the relationships between viewing distance and pupil drift of each eye separately, with the measurements often being taken at the same time. In some embodiments, a separate sensor may be provided for measuring pupil size, center location, and/or the like of the other eye. In other embodiments, the same sensor may be coupled to the other eye measurement position by the other sensor optical path, so that one sensor measures characteristics of both pupils. The sensor will often comprise at least one image capture device such as a charge couple device ("CCD") sensitive to infrared ("IR") light, or the like. When a single image capture device is used, a sensor surface of the image capture device may be separated into portions associated with each eye, or images generated thereon may alternate between the left and right eyes of the patient.

In binocular pupilometer embodiments, optical axes may extend from adjacent each eye measurement location toward the viewing target. A vergence angle between the first and second optical axes may change when the viewing target changes between a near viewing configuration and a far viewing configuration. Accommodating such changes in vergence angle may help provide a more natural physiological response to changes in viewing distance, and may thereby enhance pupil size and/or pupil drift measurements with changes in viewing distances.

In many embodiments, the optical path will image at least a sufficient portion of the pupil and an outer iris boundary of the eye onto an image detection surface of the image capture device. This may allow the pupilometer to determine a center of the pupil relative to a center of the outer iris boundary. Optionally, a variable brightness illumination source may be optically coupled to the eye measurement location. The processor can be coupled to the variable illumination source so as to determine a relationship between illumination of the eye and pupil drift or pupil size. The processor may record a plurality of relative pupil centers and associated pupil sizes and viewing distances.

In another aspect, the invention provides a binocular pupilometer comprising an image capture system and a first sensing optical path coupling the image capture system with a first eye measurement location. The first sensing optical path may have a first optical axis extending from the first eye location. A second sensing optical path may couple the image capture system with a second eye measurement location. The second sensing optical path may have a second optical axis extending from the second eye location. A variable distance viewing target system will have a target image as well as a first configuration and a second configuration. The target system will have a first viewing distance between the first and second eye locations and the target image when in the first configuration. Similarly, the target system will have a second optical viewing distance between the second image and the first and second eye locations when in the second configuration. The second viewing distance is greater than the first viewing distance, and a vergence angle between the first optical axis and the second optical axis varies when the target system changes between the first configuration and the second configuration. A processor is coupled to the image capture system and the viewing target system. The processor is configured to determine a relationship between a change in viewing distance between the eye and the viewing target, and a pupil drift of a pupil of an eye disposed at each eye location.

In another aspect, the invention provides a pupil measurement method comprising capturing a first image of a first eye while the first eye is viewing at a first viewing distance. A second image of the first eye is captured while the first eye is viewing at a second viewing distance. The second viewing distance is different than the first viewing distance. Pupil center drift of the first eye is determined from the first and second captured images of the first eye.

In many embodiments, first and second images of a second eye will be captured while the second eye is viewing at the first and second viewing distances, respectively. The eyes may be viewing at similar distances simultaneously. Pupil center drift of the second eye may be determined from the first and second captured images of the second eye. A vergence angle between optical axes of the first and second eye may change with the changes in viewing distance.

Pupil center drift may be determined by determining a first center of a first pupil of the first eye relative to a center of an outer iris boundary of the first eye from the first image. A second center of the pupil of the first eye relative to the center of the outer iris boundary of the first eye may similarly be determined from the second image. The eye will often move between the acquiring of the first and second images.

Pupil size at the first and second viewing distances will often be measured, and intermediate distances (optionally comprising one or more intermediate distance, and in some embodiments including a continuous range of intermediate distances) may be used for measurements. Variations in illumination brightness may be provided so as to determine a relationship between brightness and pupil size at differing viewing distances.

DETAILED DESCRIPTION OF THE INVENTION

The present invention generally provides improved devices, systems, and methods for measuring characteristics of the eye, particularly under varying viewing conditions. In exemplary embodiments, the invention provides pupilometers capable of measuring both pupil size and pupil center drift as a function of varying viewing distances. The device will often use one or two cameras, and will generally have an optical train for each camera which provides a field of view that is sufficient to capture a sufficient portion of the outer boundary of the iris so as to determine the iris center. Image processing software will typically identify both the iris and pupil boundaries and centers, and the size and relative center positions will be computed. Since the iris center location is substantially independent of the pupil size, the pupil center can be tracked in reference to the iris center.

Along with measurements in pupil drift and pupil size, the present invention may also provide additional characteristic measurements with changes in viewing distance, illumination or brightness, or the like. For example, measurements of the roundness of the pupil may be obtained, hysteresis or differences between the physiological characteristics of the eye when viewing conditions are changing in one direction (for example, from a far viewing distance to an intermediate viewing distance) versus another direction (in our example, changing from a near viewing distance to the intermediate viewing distance), In some embodiments, response time or delays between changes in viewing conditions and, physiological responses, differences between the two eyes of a patient, and/or the like may be determined. Hence, although the initial application for the present invention may be for development or tailoring of presbyopia prescriptions, the invention may also find applications in other fields, such as measuring anisocoria, detecting drug abuse and/or opiate addiction, and the like.

Figure 1:
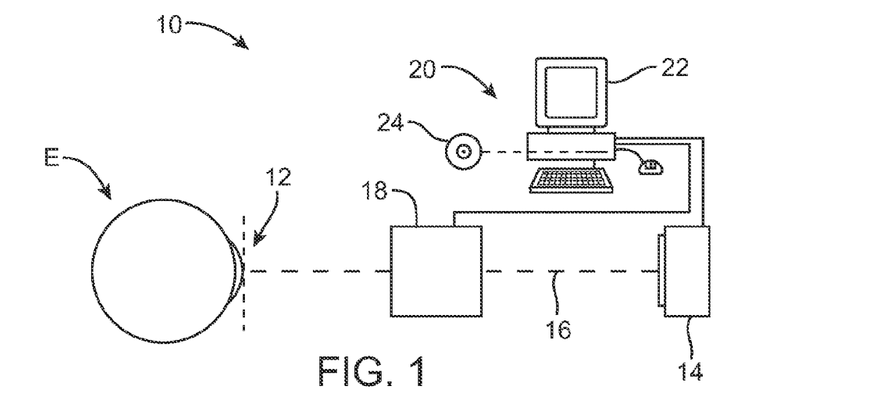
FIG. 1 schematically illustrates a pupilometer system for measuring pupil characteristics such as pupil center drift, pupil size, and/or the like with changes in viewing distance.

Referring now to FIG. 1, pupilometer 10 generally measures pupil characteristics of an eye E. Eye E will generally be disposed at an eye location 12, and will be coupled to an optical sensor such as camera 14 by an optical path 16. A variable distance viewing target system 18 presents a viewing target eye E, the target being at a variable optical viewing distance from eye location 12. The viewing target system 18 and camera 14 are coupled to a processor 20.

Figure 2:
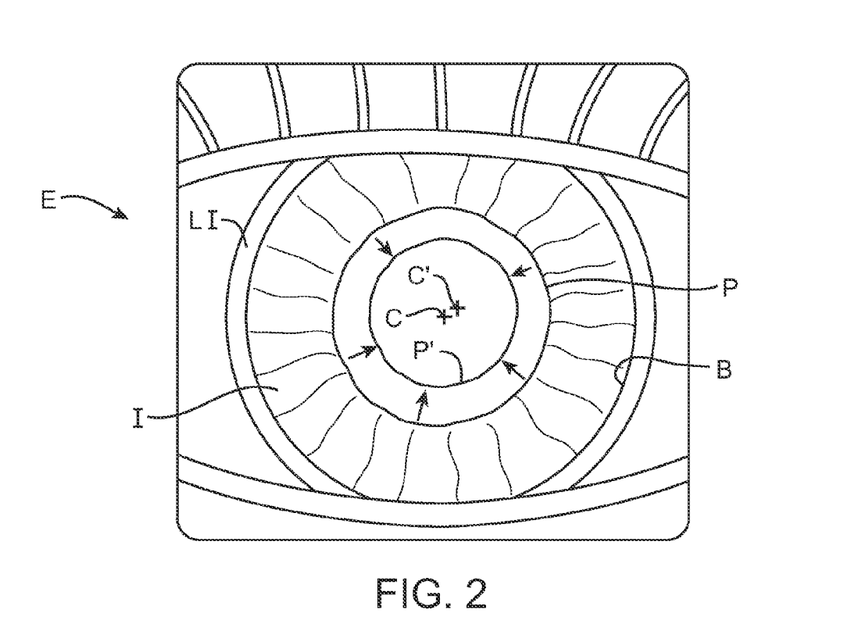
FIG. 2 illustrates an image captured by an image capture device of the system of FIG. 1, and also shows changes in pupil center location or pupil drift.

Referring now to FIGS. 1 and 2, viewing target system 18 will typically have a near viewing configuration and a far viewing configuration, with the target being displayed to eye E at viewing distances which change with the change in configuration of the target system. The eye E undergoes a variety of physiological changes with change in viewing distances. In a young emmetropic eye, ciliary muscles change a shape of the lens of the eye to change its optical power as the viewing distance changes. Additionally, the size of a pupil P of eye E varies with changes in the viewing distance. More specifically, pupil P contracts when the patient's focus changes between viewing a target at a relatively far distance to one at a nearer distance. Pupil P also contracts and/or expands with changes in brightness or illumination, with these changes in illumination optionally including changes in the brightness of the object or target being viewed, changes in the ambient light around the viewing target, and the like.

Along with changes in the overall size of pupil P when the eye E is subjected to different viewing conditions, the location of the pupil center C may also change. It should be noted that this change in location of the pupil center may be separate from and in addition to any overall movement of the eye. In other words, even if the eye E were to remain at an overall fixed location in space so that the cornea and the retina of the eye did not move, as the pupil P contracts from a first pupil configuration to a smaller pupil configuration P', the center C of the pupil may undergo a corresponding change in location to a new pupil center C'. This change in pupil center location is encompassed within the term "pupil center drift" as that term is used herein.

In the above description of pupil center drift, it was assumed that the overall eye E was not moving. The eye, however, does move. Also, when a person goes from looking at an object at a far distance to an object at a very close distance, the eyes gradually turn inward so that each eye is pointed toward the same location in space. By accommodating and providing for this change in vergence angle, pupilometer 10 may provide enhanced physiological measurement accuracy for changes in viewing distance. Along with voluntary movements of the eye as the patient looks at targets in different locations, the eye also undergoes involuntary movements. In other words, even when the patient is holding steady fixation on a visual target, eye movement still occurs. This involuntary motion will often include two-dimensional lateral movement of the pupil P as the eye rotates in its socket, cyclo-torsional rotation of the eye about its optical axis, and the like. These movements can be quite rapid and of significant size when attempting to measure the changes in pupil center location relative to the adjacent structures of the eye.

So as to allow accurate analysis of the optical properties of the eye when the pupil changes configuration from viewing at a far distance P to a near viewing configuration P', it will often be advantageous to measure the change in pupil center C from its initial position to a revised center location C' relative to some other tissue of eye E. Toward that end, center location C will often be measured relative to some visible reference structure on the eye, and ideally relative to the outer iris boundary B. The outer iris boundary is generally adjacent to a limbus LI of the eye. The limbus is the interface between the clear cornea and the white sclera of the eye. The limbus, however, is more of a transition zone between the cornea and the sclera, rather than a sharp boundary. Additionally, the scleral tissues at the interface with the cornea may be clear, so that the limbus may, at least in part, comprise the interface between two clear tissues. For these reasons, there may be advantages in making use of the outer boundary B of iris I as a reference location for monitoring pupil center drift.

Referring still to FIGS. 1 and 2, FIG. 2 generally shows an image of eye E as obtained by camera 14 during use of system 10 (along with a superimposed contracted pupil P', pupil center locations C, C', and the like). Camera 14 will generally comprise an image capture device or other optical sensor capable of detecting optical information sufficient for measurement of the pupil center location, pupil size, outer iris boundary B size and/or location, the location of other additional or alternative reference structures on the eye, and the like. In the exemplary embodiment, camera 14 comprises a charge couple device ("CCD") which is sensitive to infrared light.

Eye location 12 will generally be defined at least in part by a structure to be engaged by tissues around eye E, such as an eye cup or the like. In binocular versions of pupilometer 10, mechanisms which allow variations in distances between the eyes will often be provided, and the optical path 16 from the eye location 12 to camera 14 may be isolated from a surrounding room environment (and optionally isolated from at least a portion of the other optical path of a binocular pupilometer) using a shield, housing, drape, or the like.

Optical path 16 will often include additional optical imaging elements which are omitted from the simplified schematic of FIG. 1, including imaging lenses and the like, so as to image an iris I of eye E onto an image sensing surface of camera 14. Additional imaging components, such as apertures, filters, beam splitters, and the like may be used at least in part to define optical path 16, and the optical components will typically be held in place by an appropriate metallic or polymer support structure, which may be integrated into a housing extending from an eye cup adjacent eye location 12 to and/or beyond camera 14.

Camera 14 will typically comprise a CCD sensitive to infrared light, although a wide variety of alternative image capture structures may also be employed, including complementary metal-oxide semiconductor ("CMOS") image capture devices, HRDC image capture devices, and the like. Camera 14 may comprise, for example, a GW-902H model camera commercialized by GENWAC, INC. of New York and manufactured by WATEC CO., LTD. of Japan, which may take images using IR illumination with a wavelength of 880 nm. A variety of alternative cameras, imaging structures, or other sensors might also be used, including a GW-902B model camera from GENWAC; a Teli CE camera which may take images using IR illumination with a wavelength of 940 nm, and/or another camera selected from those commercialized as the CS8300B series by TOKYO ELECTRONIC INDUSTRY CO., LTD of Japan; a 4900 model series camera commercialized by COHU, INC., Electronics Division of San Diego; and the like. Optical path 16 will typically image a field of view of at least about 10.5 mm by 14.0 mm (measured at the plane of the iris of the eye), onto the image sensing surface, so as to image a sufficient portion of the iris with camera 14.

Processor 20 of pupilometer 10 will often comprise a personal computer, as illustrated in FIG. 1. Processor 20 will typically include a display 22 for showing an image of the structures of the eye, graphical representations of the pupil drift and any other physiological characteristic measurements, and the like. Processor 20 will typically include a tangible media 24 embodying a machine readable code with programming instructions and/or data for implementing the method steps described herein. Tangible media 24 may comprise a magnetic recording media such as a floppy disk or magnetic tape, an optical recording media such as a CD or a DVD, an electronic media or memory such as a RAM or ROM, a non-volatile memory such as a USB memory stick device, or the like. In some embodiments, the machine readable code and/or data may be transmitted via an Internet, an intranet, a wireless transmission device, an optical network or cable, an electrical coaxial or twisted pair cable, or the like. When in the form of a personal computer, processor 20 will typically include user input devices such as a keyboard and/or mouse, input and output ports, software such as an operating system and a pupilometer user interface. Alternative processor structures might also be used, including specialized processor boards, distributed data software and/or hardware arrangements, and the like.

When pupilometer 10 is in use, eye E will often be illuminated with an illumination source have a wavelength suitable for imaging of the eye by camera 14. For example, eye E may be illuminated by one or more light-emitting diodes (LEDs). Illumination may also be provided by variable distance target system 18, optionally by changing a brightness of a viewing target at a desired optical distance from the eye. In many embodiments, both the viewing distance and brightness of the viewing target or other variable illumination will be controlled by processor 20 using command signals sent to variable distance target 18 and/or any additional illumination source. Imaging signals will generally be generated by camera 14 and transmitted to processor 20.

Under infrared illumination, the pupil P of eye E will appear relatively dark to camera 14, as the infrared energy is not directly reflected by the clear corneal structure. The iris I surrounding the pupil P will present a much light shade to camera 14, with the white scleral tissue surrounding the iris presenting a still lighter shade. The relatively high contrast borders between the pupil and iris, and between the outer iris boundary and the surrounding tissues have a sufficiently high contrast image for determining pupil and iris size and center location.

Referring now to FIGS. 1-4B, a location of the iris I (and all other tissues of the eye E) will change with saccadic and other movements of the eye. While eye E is viewing at a first, relatively near viewing distance (as determined by variable viewing target 18 under the command of processor 20), image capture device 14 obtains an image of the eye. Using the difference in relative contrast between the pupil P and surrounding iris I, camera 14 determines a diameter of pupil P and identifies a center location PC1. Similarly, using the same image captured by camera 14, processor 20 also determines a diameter of the outer iris boundary B and a location of the boundary center BC1, generally by using the contrast differential between the outer iris boundary and the surrounding tissues. Based on the difference in location between the outer iris boundary center BC1 and the pupil center boundary PC1, processor 20 identifies a horizontal center difference $\Delta x$ and a vertical center difference $\Delta y$. For a first image at a relatively near viewing distance as shown in FIG. A, the identified $\Delta x1$ and $\Delta y1$ are plotted as illustrated in FIGS. 3A and 3B.

Figure 3A:
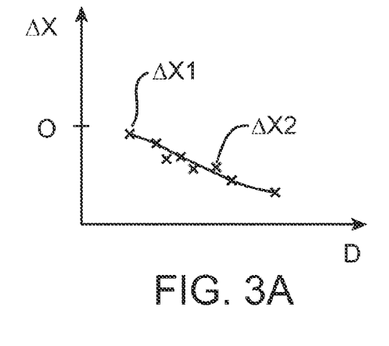
FIGS. 3A and 3B graphically illustrate a relationship between pupil center drift and viewing distance for the left eye and right eye of a patient, respectively.
Figure 3B:
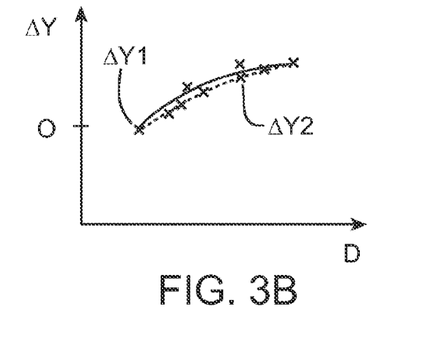
Figure 4A:
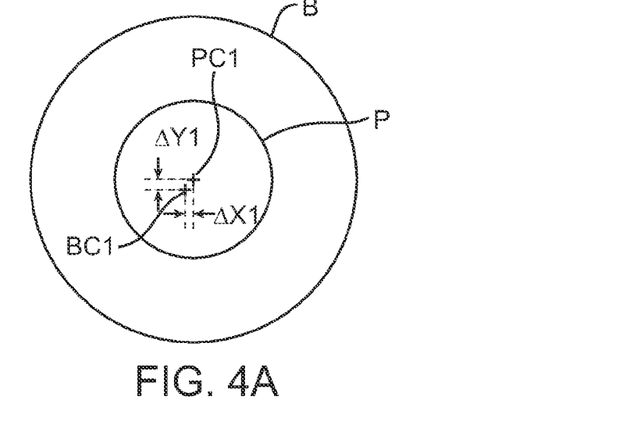
FIGS. 4A and 4B schematically illustrate methods for determining pupil center drift from different images taken at different viewing distances by identifying centers of a pupil and an outer iris boundary.
Figure 4B:
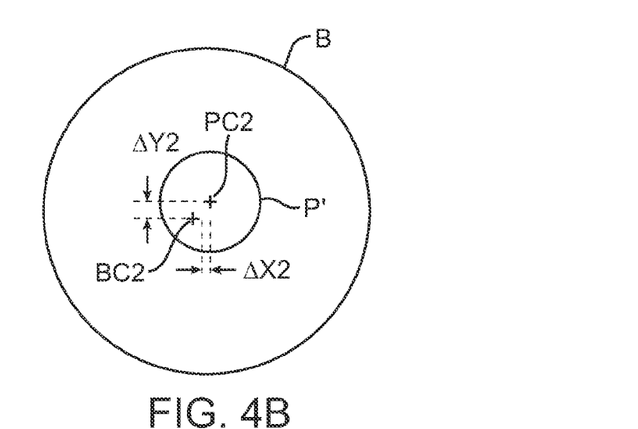

Referring now to FIGS. 2, 3A and B, and 4B, a measurement taken with the variable distance viewing target at a nearer optical viewing distance results in constriction of the pupil to a smaller pupil size P'. Processor 20 once again determines a size and center location of the constricted pupil PC2 relative to the concurrent outer iris boundary center BC2 so as to determine new horizontal and vertical center offsets $\Delta x2$ and $\Delta y2$. By measuring a series of different viewing distances, horizontal and vertical pupil center drift with changing viewing distance D may be plotted as shown in FIGS. 3A and 3B.

Image processing software for use in determining the size and central location of pupil P and outer iris boundary B is commercially available from a number of sources. A variety of image processing software packages may be used, including (for example) INTEL IMAGE processing libraries or the like. Processors suitable for pupilometer include PCs having the power of an INTEL Pentium® processor. Many of the processors could also be used, including those running the MacOS operating system from APPLE COMPUTERS, INC., a custom DSP device, or the like. Alternative embodiments may make use of software modified from that of a commercially available pupilometer, such as the P2000 line of pupilometers sold by PROCYON of the United Kingdom.

So as to effectively measure pupil center drift, pupil size, pupil roundness, and other physiological changes throughout a range of viewing distances, it will often be advantageous to include a variable distance viewing target system 18 capable of varying an optical viewing distance between eye location 12 and a target from no more than about 1 meter to at least about 3, and often at least about 5 meters. Exemplary variable distance viewing target systems 18 will provide a plurality of intermediate viewing distances between a nearest viewing distance and a farthest viewing distance. In some embodiments, particularly where hysteresis appears to be an issue, processor 20 may calculate different relationships between pupil center drift and viewing distance, with one relationship for pupil constriction (going from a far viewing distance to a near viewing distance) and one for pupil expansion (going from a near viewing distance to a far viewing distance). Still further pupil center drift measurements may be recorded and/or analyzed, including pupil center drift at differing viewing brightnesses, such as at photopic viewing conditions, scotopic viewing conditions, and intermediate light viewing conditions.

Figure 5:
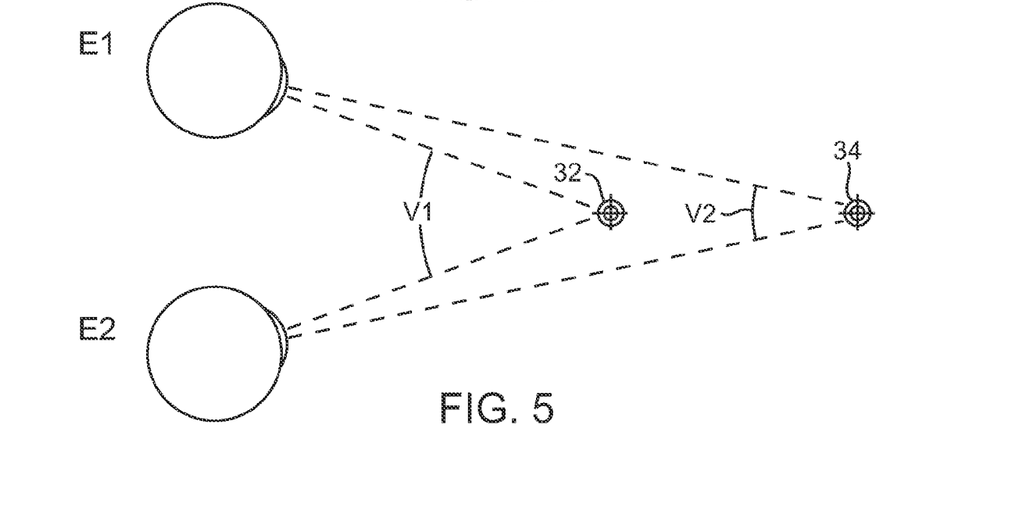
FIG. 5 schematically illustrates changes in vergence angle with changes in viewing distances.

Referring now to FIG. 5, when a patient having eyes E1 and E2 is viewing a near-distance viewing target 32, the optical axes of the eyes define a first vergence angle V1. As the eyes shift in viewing distance from the near viewing target 32 to the far viewing target 34, the vergence angle of eyes E1, E2 changes to a second vergence angle V2. The pupilometers described herein will preferably accommodate such changes in the vergence angle with changes in viewing distance, particularly for binocular versions of the pupilometer.

Figure 6:
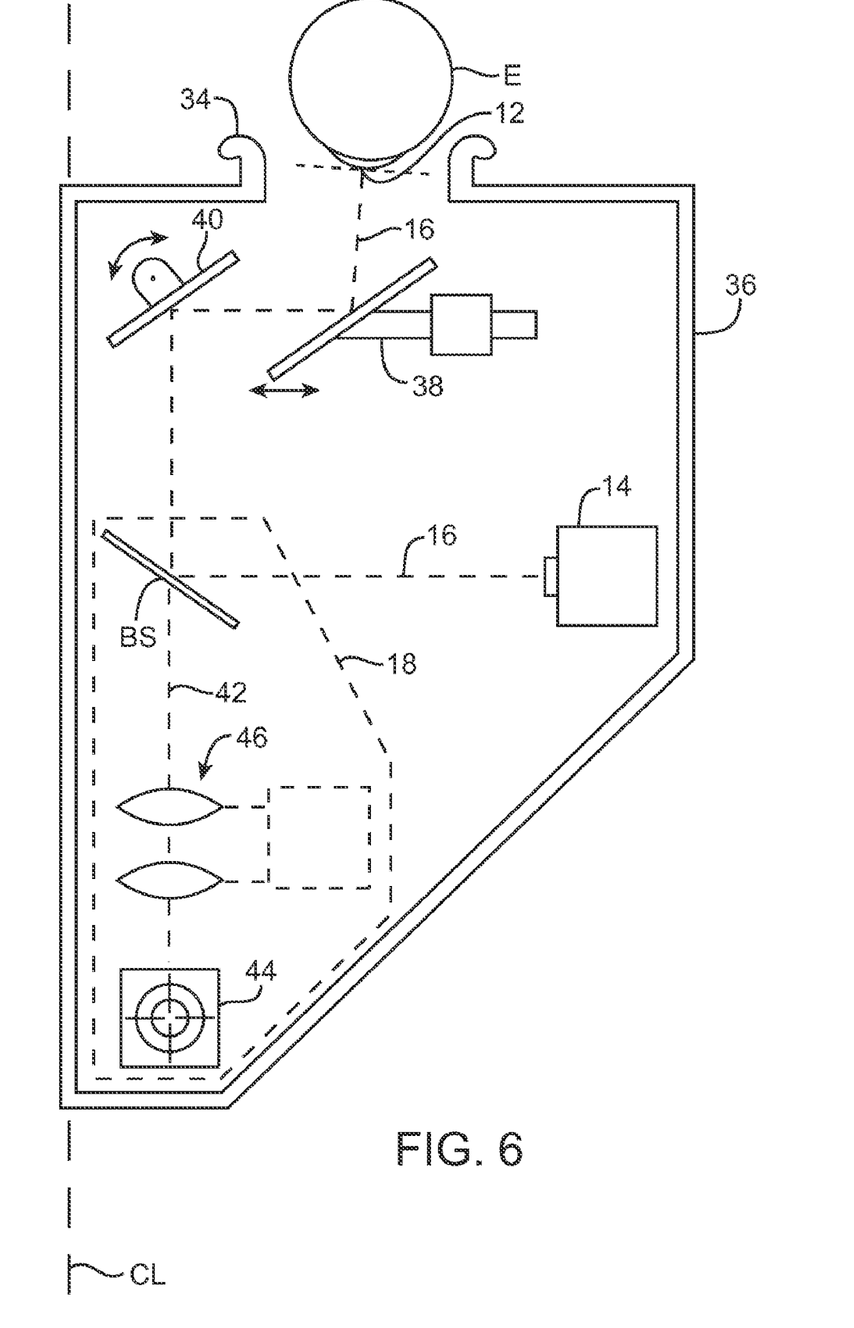
FIG. 6 schematically illustrates some of the optical elements and other components of a pupilometer.

Referring now to FIG. 6, optical components of pupilometer 10 are shown in more detail. As described above, an optical path 16 extends from an eye location 12 to camera 14. Eye location 12 is defined by an eye cup 34 which engages tissue around eye E. A housing 36 isolates the optical components of the eye and the optical pans of the pupilometer from ambient light, and structurally supports the optical components of the pupilometer. Optionally, housing 36 may form one half of a binocular pupilometer, with the other portion of the pupilometer being disposed on the other side of a center line CL for the patient's other eye.

So as to accommodate changes in vergence angle of eye E, optical path 16 is reflected by a movable mirror system including a translatable mirror 38 and/or an angularly displaceable mirror 40. These movable mirrors may be driven by galvanometer or other electrically driven actuators, often per signals received from processor 20. Other embodiments may make use of manually repositioned mirrors which change position and/or angle in response to manual inputs from outside housing 36.

In the embodiment of FIG. 6, a portion of the imaging optical path 16 is separated from a target optical path 42 by a beam splitter BS of variable viewing distance system 18. In other embodiments, the target optical path and imaging optical path may be separated along substantially their entire length, particularly when imaging of the eye takes place from off the optical axis of the eye. An off-axis eye tracker which might be modified to measure pupil center drift is described in more detail in U.S. patent application Ser. No. 09/545,240, entitled "Two Camera Off-Axis Eye Tracker for Laser Eye Surgery" as filed on Apr. 7, 2000, now issued as U.S. Pat. No. 6,322,216, the full disclosure of which is incorporated herein by reference.

In the schematic illustration of FIG. 6, along with a viewing target image 44, variable distance viewing system 18 includes a zoom lens system 46 for changing an optical viewing distance between eye location 12 and target 44. Zoom lens system 46 will include motors or the like for repositioning lenses so as to change the optical path distance in response to signals form the processor. Alternative embodiments may have a manual system for actuating the zoom lenses with a zoom position sensor providing signals to the processor, or may rely on manual input of the zoom position.

Alternative variable distance viewing targets are also possible, including systems which rely on removal and replacement of one or more optical components. For example, one or more of the lens of the variable distance viewing system may be mounted on a turret so that a first lens can be rotated out of the target optical path 42 and replaced by another lens of the turret. In some embodiments, target image 44 may simply be moved a greater distance away from other optical components, or may be replaced by another target at a farther viewing distance.

Figure 7:
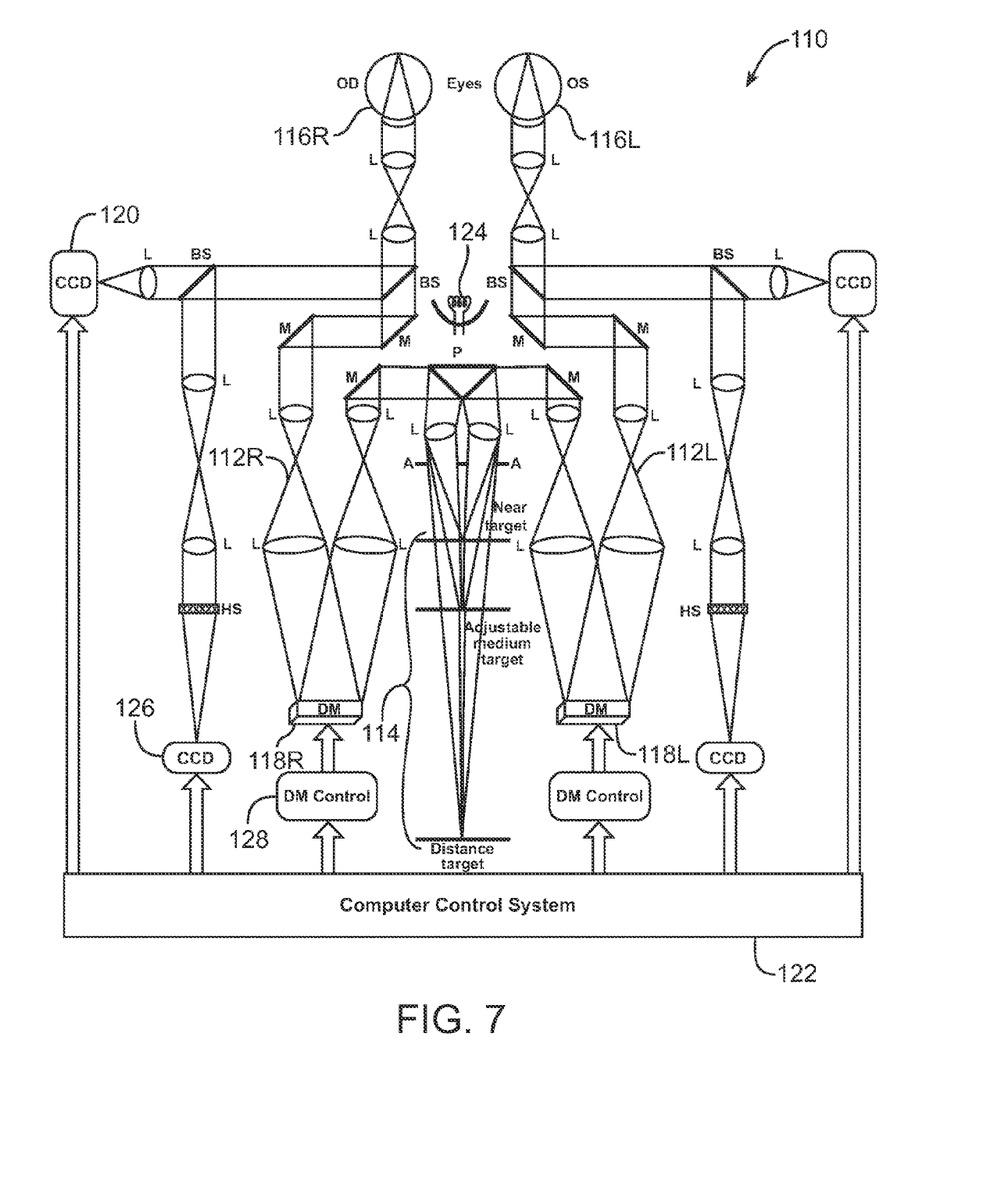
FIG. 7 illustrates an alternative embodiment of a binocular pupilometer.

Still further alternative pupilometer structures may be employed, including that schematically illustrated in FIG. 7. The optical components of pupilometer 110 are described in more detail in U.S. patent application Ser. No. 10/872,331, filed on Jun. 17, 2004, and entitled "Correction of Presbyopia Using Adaptive Optics and Associated Methods", the full disclosure of which is incorporated herein by reference. Along with allowing imaging and measurement of the pupils or other physiological changes the eyes in response to changes in viewing distance, pupilometer 110 includes deformable mirrors and Hartmann-Shack wavefront sensors for modeling refractive changes to the eyes and measuring optical aberrations of the eyes. More specifically, pupilometer 110 generally includes an optical path 112R coupling an adjustable target 114 with a right eye 116R of a patient. A similar optical path 112L couples adjustable target 114 with a left eye 116L, thereby providing a binocular viewing system. Adjustable mirrors or the like such as those described above regarding FIG. 6 may be included so as to accommodate changes in vergence angle between the eyes. As the components of the optical path, sensors, and the like of pupilometer 110 along the right optical path 112R are generally similar to those of the left optical path 112L, only the right side need be described to understand the structure and use of the apparatus.

Optical path 112 includes a series of lenses L and mirrors M optically coupling adjustable target 114 to right eye 116R via a deformable mirror 118R. A Hartmann-Shack wavefront sensor HS is coupled to optical path 112R by a beam splitter BS for measurement of aberrations of eye 116R. A sensor 120 is also coupled to the optical path 112R by one or more beam splitters BS for measurement of a size of a pupil of eye 116R, measurement of pupil center drift, and the like.

Adjustable target 114 transmits an image along optical path 112R, with the light being profiled by an aperture A having a field stop. The light is collimated by an adjustable focal length lens L before being directed along the optical path using a prism P. At the end of the optical path adjacent eye 116R, the light is re-collimated by lenses L to go through the optics of the eye, primarily the cornea and the lens of the eye, so as to form an image on the retina.

When pupilometer 110 is used for measuring pupil center drift, deformable mirror 118R may be in a flat configuration or may be configured so as to compensate for refractive errors of the eye 116R. Regardless, the patient will view the viewing target 114 at the desired viewing distance. Sensor 120, which will often comprise a CCD or the like as described above regarding camera 14, will obtain an image of eye 116R.

Sensor 120 will transmit appropriate image signals to computer control system 122 so as to allow the pupil center location relative to the outer pupil boundary (or the like) to be determined, along with pupil size or any other desired physiological characteristics. Adjustable viewing target 114 may then be revised to a new viewing target distance, and the process repeated.

As described in more detail in U.S. patent application Ser. No. 10/872,331, computer control system 122 may drive deformable mirror 118R in response to signals from another CCD 126 associated with the Hartmann-Shack sensor HS. This may allow the deformable mirror to compensate for and measure the ocular aberration of the eyes. Ambient lighting 124 may also be under the control of computer system 122 so as to measure pupil properties at different lighting conditions.

While the exemplary embodiments have been described in some detail for clarity of understanding and by way of example, a variety of adaptations, modifications, and changes will be obvious to those of skill in the art. For example, the processor may employ dynamic thresholding in measurements of the pupil and outer iris boundary. Rather than estimating the shape of the outer iris boundary from only a portion of that structure, the method may employ a speculum in the eye during pupil center drift measurements so that the entire outer iris boundary is within the field of view of the image capture device. A single camera may be used to measure pupils of both eyes in binocular systems, with the optical paths from the eyes optionally being separated adjacent the image sensing surface of the camera by a shield or the like, as described in U.S. Pat. No. 5,784,145, the full disclosure of which is incorporated herein by reference. Hence, the scope of the present invention is limited solely by the appended claims.

what is claimed is:

1. A pupilometer comprising:
   an optical sensor including an image capture device having an image detection surface;
   a sensing optical path coupling the sensor with an eye measurement location, wherein the sensing optical path images at least a sufficient portion of the pupil and the outer iris boundary of an eye disposed at the eye measurement location onto the image detection surface of the image capture device so that the pupilometer can determine a center of the pupil relative to a center of the outer iris boundary;
   a variable brightness illumination source; and,
   a processor coupled to the optical sensor and the variable brightness illumination source, the processor having tangible media embodying machine-readable code for determining a relationship between:
      changes in brightness of illumination at the eye measurement location, and
      location of the pupil center relative to the outer iris boundary of the eye disposed at the eye measurement location wherein the processor further comprises a display for showing a graphical representation of the relationship; and wherein the graphical representation of the relationship comprises a plot of pupil center location versus brightness level, the plot comprising a plurality of plotted data points, the plurality comprising a data point from each of at least three differing brightness levels measured at the eye measurement location.

2. The pupilometer of claim 1, wherein the sensing optical path images at least a sufficient portion of the pupil and the outer iris boundary of the eye onto the image detection surface of the image capture device so that the pupilometer can determine a size or shape of the pupil.

3. The pupilometer of claim 1, wherein the variable brightness illumination source is in optical communication with the eye measurement location.

4. The pupilometer of claim 1, wherein the variable brightness illumination source comprises ambient lighting.

5. The pupilometer of claim 1, wherein the variable brightness illumination source comprises an illumination source having differing levels of brightness, the differing levels of brightness comprising a brightness level sufficient to produce photopic viewing conditions and a brightness level sufficient to produce scotopic viewing conditions.

6. The pupilometer of claim 5, wherein the differing levels of brightness further comprise a brightness level sufficient to produce intermediate light viewing conditions.

7. The pupilometer of claim 5, further comprising a viewing target.

8. The pupilometer of claim 7, wherein the variable brightness illumination source is in optical communication with the viewing target sufficient to provide the differing levels of brightness to the eye measurement location by illuminating the target.

9. The pupilometer of claim 7, wherein the viewing target comprises a variable distance viewing target system having a near viewing configuration and a far viewing configuration.

10. The pupilometer of claim 9, wherein the processor is coupled to the variable viewing target system, the processor having tangible media embodying machine-readable code for determining a relationship between:
    changes in brightness of illumination at the eye measurement location;
    the location of the pupil center or pupil drift; and
    a viewing distance between the eye measurement location and the viewing target.

11. The pupilometer of claim 10, wherein the variable brightness illumination source comprises an ambient light source or a light source in optical communication with the viewing target to illuminate the target.

12. The pupilometer of claim 1, wherein the pupilometer comprises a binocular pupilometer with another sensing optical path coupled to another eye measurement location, the processor configured to determine another relationship between changes in brightness and the location of the pupil center relative to the outer iris boundary of another eye of the patient at the other eye measurement location while the first eye is at the eye measurement location.

13. The pupilometer of claim 12, further comprising another optical sensor in the other sensing optical path, the other sensor coupled to the processor and the other eye measurement location.

14. The pupilometer of claim 1, wherein the image capture device comprises a CCD sensitive to IR light.

15. The pupilometer of claim 1, wherein the processor records a plurality of pupil center locations and associated brightness levels.

16. The pupilometer of claim 2, wherein the processor records a plurality of pupil sizes or shapes and associated brightness levels.

17. The pupilometer of claim 9, wherein the processor records a plurality of pupil center locations and associated levels of brightness and viewing distances.

18. The pupilometer of claim 1, wherein the differing brightness levels comprise a scotopic, a photopic, and an intermediate viewing condition.

19. A pupil measurement method comprising:
capturing a first image of a first eye at a first brightness level of illumination;
capturing a second image of the first eye at a second brightness level of illumination, the second brightness level of illumination being different from the first brightness level of illumination;
determining a pupil center location relative to the outer iris boundary of the first eye from the first and second captured images of the first eye;
determining a relationship between the pupil center location and the first and second brightness levels of illumination wherein determining the relationship comprises producing a graphical representation comprising a horizontal or a vertical pupil center drift plotted against a brightness level at the eye measurement location.

20. The pupil measurement method of claim 19, further comprising:
determining a size or shape of the pupil from the first and second captured images of the first eye.

21. The pupil measurement method of claim 19, wherein the first brightness level of illumination comprises a level of illumination sufficient to make the eye photopic, and wherein the second brightness level of illumination comprises a level of illumination sufficient to make the eye scotopic.

22. The pupil measurement method of claim 19, further comprising:
determining the pupil center drift relative to the center of the outer iris boundary of the first eye from the first and second capture images of the first eye, the pupil center drift being separate from any overall movement of the eye.

23. The pupil measurement method of claim 19, wherein capturing the first and second image of the first eye further comprises capturing the first and second image of the first eye while the first eye is viewing a target.

24. The pupil measurement method of claim 23, further comprising:
determining a relationship between the pupil center location, the brightness level of illumination and a distance between the eye and the viewing target.

25. The pupil measurement method of claim 23, further comprising:
determining a relationship between the size or shape of the pupil, the brightness level of illumination and a distance between the eye and the viewing target.

26. The pupil measurement method of claim 23, further comprises capturing the first image while the eye is viewing the target at a first distance from the eye and capturing the second image while the eye is viewing the target at the first distance from the eye.

27. The method of 19, wherein the relationship is based on a plurality of data points of pupil center location information from differing brightness levels.

28. The method of 27, wherein determining the relationship comprises curve fitting the plurality of data points.

29. The method of 27, wherein the plurality of data points comprise at least three data points from at least three differing brightness levels.

30. The method of 29, wherein the at least three differing brightness levels comprise a photopic, a scotopic, and an intermediate viewing condition.

31. The method of claim 19, wherein the graphical representation comprises a plurality of data points of pupil center location information from at least three differing brightness levels.

32. The method of 31, wherein the at least three differing brightness levels comprise a photopic, a scotopic, and an intermediate viewing condition.

33. The method of 31, wherein the graphical representation comprises a curve fit of the plurality of data points.

34. A pupil measurement method comprising:
capturing a first image of a first eye at a first brightness level of illumination while the eye is viewing a target at a first distance from the eye;
capturing a second image of the first eye at a second brightness level of illumination while the eye is viewing the target at the first distance from the eye, the second brightness level of illumination being different from the first brightness level of illumination;
determining a pupil center location relative to the outer iris boundary of the first eye from the first and second captured images of the first eye;
capturing a third image of the first eye at the first brightness level of illumination while the eye is viewing the target at a second distance; and
capturing a fourth image of the first eye at the second brightness level of illumination while the eye is viewing the target at the second distance, the second viewing target distance being different from the first viewing target distance.

35. The pupil measurement method of claim 34, further comprising:
determining a relationship between the pupil center location, a change in brightness levels of illumination and a change in distance between the eye and the viewing target.

36. The pupil measurement method of claim 35, further comprising:
determining a relationship between pupil size or shape, a change in brightness levels of illumination and a change in distance between the eye and the viewing target.

* * * * *